US011607217B2

(12) United States Patent
Shelton, IV et al.

(10) Patent No.: US 11,607,217 B2
(45) Date of Patent: Mar. 21, 2023

(54) SURGICAL STAPLER SHAFT FORMED OF SEGMENTS OF DIFFERENT MATERIALS

(71) Applicant: ETHICON LLC, Guaynabo, PR (US)

(72) Inventors: Frederick E. Shelton, IV, Hillsboro, OH (US); Chester O. Baxter, III, Loveland, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 630 days.

(21) Appl. No.: 16/236,696

(22) Filed: Dec. 31, 2018

(65) Prior Publication Data

US 2020/0205814 A1    Jul. 2, 2020

(51) Int. Cl.
*A61B 17/72*    (2006.01)
*A61B 17/072*   (2006.01)
(Continued)

(52) U.S. Cl.
CPC ............ *A61B 17/072* (2013.01); *B21B 17/00* (2013.01); *A61B 2017/00367* (2013.01);
(Continued)

(58) Field of Classification Search
CPC ........ A61B 17/072; A61B 2017/00367; A61B 2017/00477; A61B 2017/00526; A61B 2017/07271; B21B 17/00
(Continued)

(56) References Cited

U.S. PATENT DOCUMENTS 5,163,945 A   11/1992  Ortiz et al.
5,205,459 A   4/1993   Brinkerhoff et al.
(Continued)

FOREIGN PATENT DOCUMENTS

EP   2 807 984 A2   12/2014
EP   3 348 209 A2   7/2018
(Continued)

OTHER PUBLICATIONS

European Search Report and Written Opinion dated Jul. 16, 2020 for Application No. EP 19220003.8, 16 pgs.
(Continued)

*Primary Examiner* — Valentin Neacsu
*Assistant Examiner* — Mary C Hibbert-Copeland
(74) *Attorney, Agent, or Firm* — Frost Brown Todd LLP

(57) ABSTRACT

A surgical instrument includes an end effector and a shaft. The end effector includes a first jaw movable relative to the second jaw. The shaft extends proximally from the end effector. The shaft includes a proximal coupler, a tube, and a distal coupler. The proximal coupler includes a distal coupling feature adjacent a distal end. The tube includes proximal and distal coupling features that are adjacent the respective proximal and distal ends of the tube. The proximal coupling feature is configured to engage the distal coupling feature of the proximal coupler to securably lock the tube and the proximal coupler together. The distal coupler includes a proximal coupling feature adjacent the proximal end of the distal coupler. The proximal coupling feature of the distal coupler is configured to engage the distal coupling feature of the tube to securably lock the distal coupler and the tube together.

20 Claims, 12 Drawing Sheets

(51) Int. Cl.
*B21B 17/00* (2006.01)
*A61B 17/00* (2006.01)

(52) U.S. Cl.
CPC ............. *A61B 2017/00477* (2013.01); *A61B 2017/00526* (2013.01); *A61B 2017/07271* (2013.01)

(58) Field of Classification Search
USPC ...................................................... 227/175.1
See application file for complete search history.

(56) References Cited

U.S. PATENT DOCUMENTS

| | | | |
|---|---|---|---|
| 5,271,544 | A | 12/1993 | Fox et al. |
| 5,275,322 | A | 1/1994 | Brinkerhoff et al. |
| 5,285,945 | A | 2/1994 | Brinkerhoff et al. |
| 5,292,053 | A | 3/1994 | Bilotti et al. |
| 5,333,773 | A | 8/1994 | Main et al. |
| 5,342,373 | A | 8/1994 | Stefanchik et al. |
| 5,350,104 | A | 9/1994 | Main et al. |
| 5,403,312 | A | 4/1995 | Yates et al. |
| 5,431,668 | A | 7/1995 | Burbank, III et al. |
| 5,445,167 | A | 8/1995 | Yoon et al. |
| 5,533,661 | A | 7/1996 | Main et al. |
| 5,601,573 | A | 2/1997 | Fogelberg et al. |
| 5,951,574 | A | 9/1999 | Stefanchik et al. |
| 6,988,650 | B2 | 1/2006 | Schwemberger et al. |
| 7,000,818 | B2 | 2/2006 | Shelton, IV et al. |
| 7,134,587 | B2 | 11/2006 | Schwemberger et al. |
| 7,147,140 | B2 | 12/2006 | Wukusick et al. |
| 7,204,404 | B2 | 4/2007 | Nguyen et al. |
| 7,207,472 | B2 | 4/2007 | Wukusick et al. |
| 7,261,724 | B2 | 8/2007 | Molitor et al. |
| 7,380,696 | B2 | 6/2008 | Shelton, IV et al. |
| 7,422,139 | B2 | 9/2008 | Shelton, IV et al. |
| 7,464,849 | B2 | 12/2008 | Shelton, IV et al. |
| 7,670,334 | B2 | 3/2010 | Hueil et al. |
| 7,686,820 | B2 | 3/2010 | Huitema et al. |
| 7,699,860 | B2 | 4/2010 | Huitema et al. |
| 7,731,724 | B2 | 6/2010 | Huitema et al. |
| 7,753,245 | B2 | 7/2010 | Boudreaux et al. |
| 7,845,537 | B2 | 12/2010 | Shelton, IV et al. |
| 7,980,443 | B2 | 7/2011 | Scheib et al. |
| 8,038,686 | B2 | 10/2011 | Huitema et al. |
| 8,210,411 | B2 | 7/2012 | Yates et al. |
| 8,220,688 | B2 | 7/2012 | Laurent et al. |
| 8,262,679 | B2 | 9/2012 | Nguyen |
| 8,308,040 | B2 | 11/2012 | Huang et al. |
| 8,393,514 | B2 | 3/2013 | Shelton, IV et al. |
| 8,408,439 | B2 | 4/2013 | Huang et al. |
| 8,453,914 | B2 | 6/2013 | Laurent et al. |
| 8,490,851 | B2 | 7/2013 | Blier et al. |
| 8,517,239 | B2 | 8/2013 | Scheib et al. |
| 8,561,870 | B2 | 10/2013 | Baxter, III et al. |
| 8,608,045 | B2 | 12/2013 | Smith et al. |
| 8,733,613 | B2 | 5/2014 | Huitema et al. |
| 8,910,847 | B2 | 12/2014 | Nalagatla et al. |
| 9,072,535 | B2 | 7/2015 | Shelton, IV et al. |
| 9,101,358 | B2 | 8/2015 | Kerr et al. |
| 9,186,142 | B2 | 11/2015 | Fanelli et al. |
| 9,345,481 | B2 | 5/2016 | Hall et al. |
| 9,517,065 | B2 | 12/2016 | Simms et al. |
| 9,713,469 | B2 | 7/2017 | Leimbach et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,839,421 | B2 | 12/2017 | Zerkle et al. |
| 9,867,615 | B2 | 1/2018 | Fanelli et al. |
| 9,907,552 | B2 | 3/2018 | Measamer et al. |
| 9,936,949 | B2 | 4/2018 | Measamer et al. |
| 10,092,292 | B2 | 10/2018 | Boudreaux et al. |
| 10,856,869 | B2 | 12/2020 | Shelton, IV et al. |
| 2005/0139636 | A1 | 6/2005 | Schwemberger et al. |
| 2005/0143759 | A1 | 6/2005 | Kelly |
| 2005/0145672 | A1 | 7/2005 | Schwemberger et al. |
| 2006/0052793 | A1* | 3/2006 | Heinz ................. A61B 17/025 606/90 |
| 2007/0175955 | A1 | 8/2007 | Shelton, IV et al. |
| 2008/0308604 | A1* | 12/2008 | Timm .............. A61B 17/07207 227/175.1 |
| 2014/0239037 | A1 | 8/2014 | Boudreaux et al. |
| 2014/0263552 | A1 | 9/2014 | Hall et al. |
| 2015/0083772 | A1 | 3/2015 | Miller et al. |
| 2015/0083773 | A1 | 3/2015 | Measamer et al. |
| 2015/0083774 | A1 | 3/2015 | Measamer et al. |
| 2015/0083775 | A1 | 3/2015 | Leimbach et al. |
| 2016/0374672 | A1 | 12/2016 | Bear et al. |
| 2017/0027571 | A1 | 2/2017 | Nalagatla et al. |
| 2017/0258471 | A1 | 9/2017 | DiNardo et al. |
| 2018/0132849 | A1 | 5/2018 | Miller et al. |
| 2018/0132853 | A1 | 5/2018 | Miller et al. |
| 2018/0289372 | A1 | 10/2018 | Nie et al. |
| 2018/0310938 | A1 | 11/2018 | Kluener et al. |
| 2018/0310939 | A1 | 11/2018 | Stager et al. |
| 2019/0183592 | A1* | 6/2019 | Shelton, IV ......... A61B 17/282 |

FOREIGN PATENT DOCUMENTS

| | | |
|---|---|---|
| EP | 3 539 487 A1 | 9/2019 |
| EP | 3 545 881 A1 | 10/2019 |
| WO | WO 2015/127250 A1 | 8/2015 |
| WO | WO 2018/049211 A1 | 3/2018 |

OTHER PUBLICATIONS

International Search Report and Written Opinion dated Jul. 17, 2020 for Application No. PCT/IB2019/061244, 21 pgs.

* cited by examiner

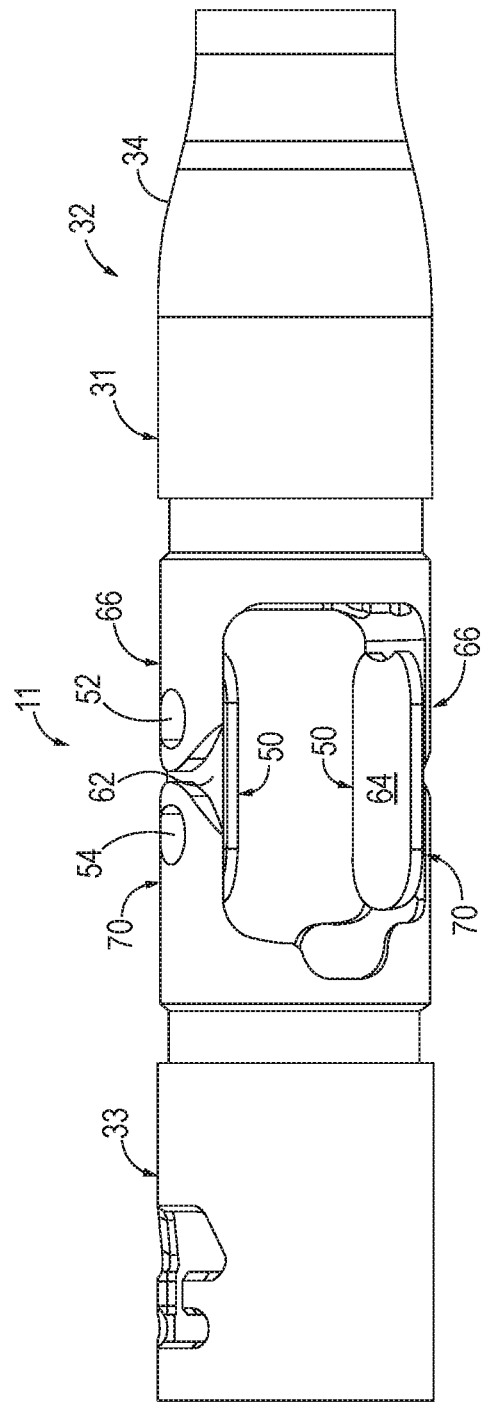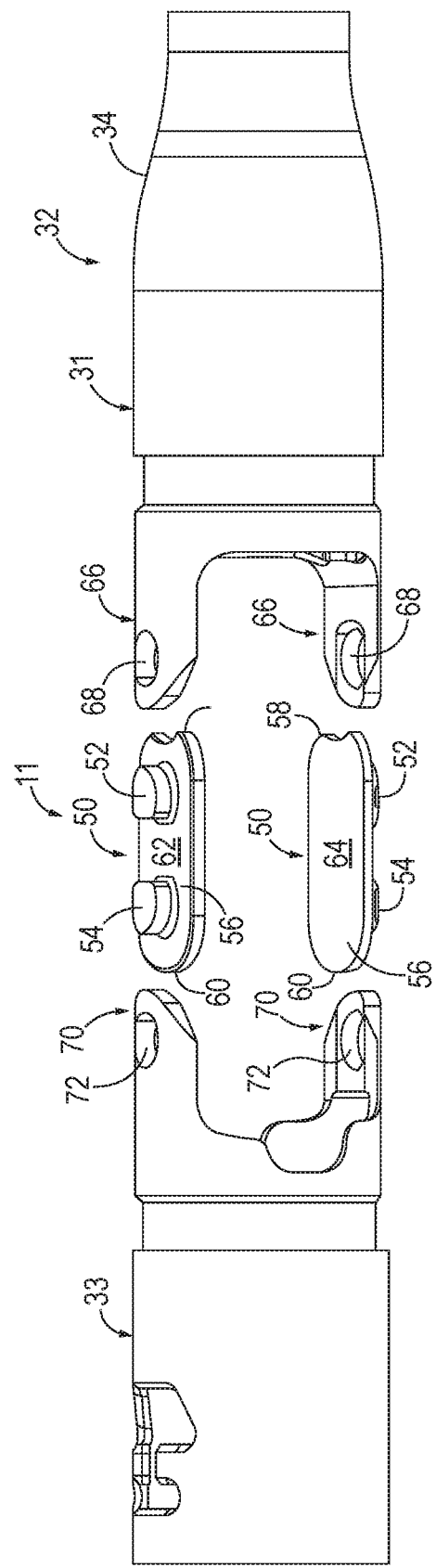
FIG. 3A
FIG. 3B

SURGICAL STAPLER SHAFT FORMED OF SEGMENTS OF DIFFERENT MATERIALS

BACKGROUND

Endoscopic surgical instruments may include a shaft between the end effector and a handle portion, which is manipulated by the clinician. Such a shaft may enable insertion through a trocar to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 3A depicts a side view of the closure tube coupled with a closure ring of FIG. 2 using closure links;

FIG. 3B depicts an exploded side view of the coupling of the closure tube to the closure ring using the closure links of FIG. 3A;

Figure 1:
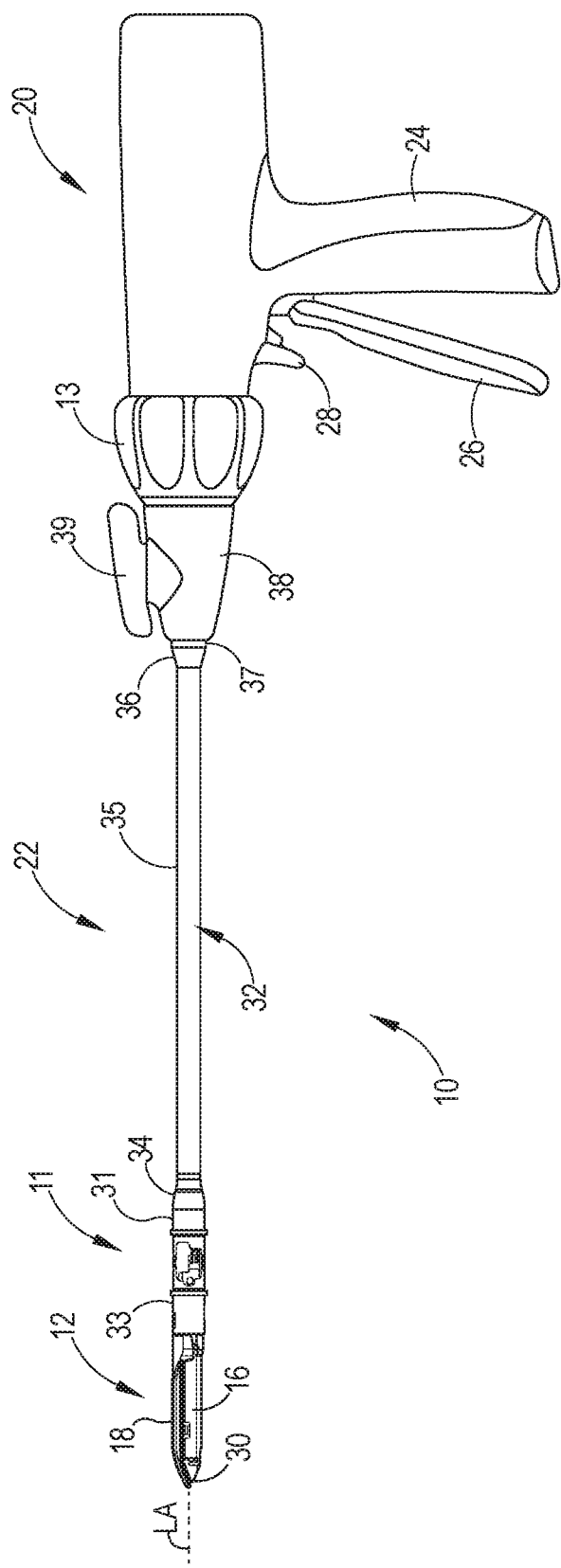
FIG. 1 depicts a side view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. SURGICAL INSTRUMENT HAVING A MULTI-DIAMETER SHAFT

In some instances, it may be desirable to increase the range of movement and positioning ability of a surgical instrument. For example, when the shaft of the surgical instrument is inserted through a thoracotomy, the shaft is positioned between a patient's ribs or elsewhere. It may be desirable to angle or move the shaft without prying or otherwise damaging the patient's ribs or soft tissue around the thoracotomy. Accordingly, it is desirable to provide a surgical instrument having multi-diameter shaft features that allow for increased range of movement or positioning ability of the instrument. The examples below include several merely illustrative versions of multi-diameter shaft features that may be readily introduced to a surgical instrument.

A. Exemplary Stapling Instrument

FIGS. 1-3B depict a surgical stapling and severing instrument (10) that includes a multi-diameter shaft (22). Instrument (10) is sized for insertion through a trocar cannula or an incision (e.g., thoracotomy, etc.) to a surgical site in a patient for performing a surgical procedure. Shaft (22) may be constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein. Shaft (22) distally terminates in an articulation joint (11) which is further coupled with an end effector (12). End effector (12) comprises a lower jaw (16) and a pivotable anvil (18). Handle portion (20) comprises a pistol grip (24) and a closure trigger (26). Closure trigger (26) is pivotable toward pistol grip (24) to cause clamping, or closing, of the anvil (18) toward lower jaw (16) of end effector (12). Firing trigger (28) of handle portion (20) may be actuated to translate a firing beam distally to cause the stapling and severing of clamped tissue in end effector (12). Thereafter, triggers (26, 28) may be released to release the tissue from end effector (12).

Handle portion (20) comprises a rotation knob (13) and a control knob (39). Rotation knob (13) may be rotated to rotate shaft (22) and end effector (12) about the longitudinal axis of shaft (22) and relative to handle portion (20) such that end effector (12) may be positioned at different rotational positions about the longitudinal axis of shaft (22) within the patient. Control knob (39) extends from handle portion (20) and may be rotated to deflect end effector (12) from the longitudinal axis of shaft (22) at articulation joint (11). Instrument (10) may interface with a person, robotic controller, or other drive method apparent to one with ordinary skill in the art in view of the teachings herein. Once articulation joint (11) and end effector (12) are inserted through the cannula passageway of a trocar, articulation joint (11) may be remotely articulated by a rotation knob (13), such that end effector (12) may be deflected from a longitudinal axis (LA) of shaft (22) at a desired angle. Articulation joint (11) and/or rotation knob (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein; and/or U.S. Pat. No. 9,795,379, the disclosure of which is incorporated by reference herein.

Lower jaw (16) may be constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; and/or U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein. Staple cartridge (30) may be constructed and operable in accordance with at least some of the teachings of U.S. Pat. No. 9,517,065, the disclosure of which is incorporated by reference herein; and/or U.S. Pat. No. 9,808,248, the disclosure of which is incorporated by reference herein. Alternatively, the foregoing components may be constructed and operable in any other suitable fashion, including but not limited to being constructed and operable in accordance with the teachings of any other patent reference cited herein.

B. Exemplary Shaft

Figure 2:
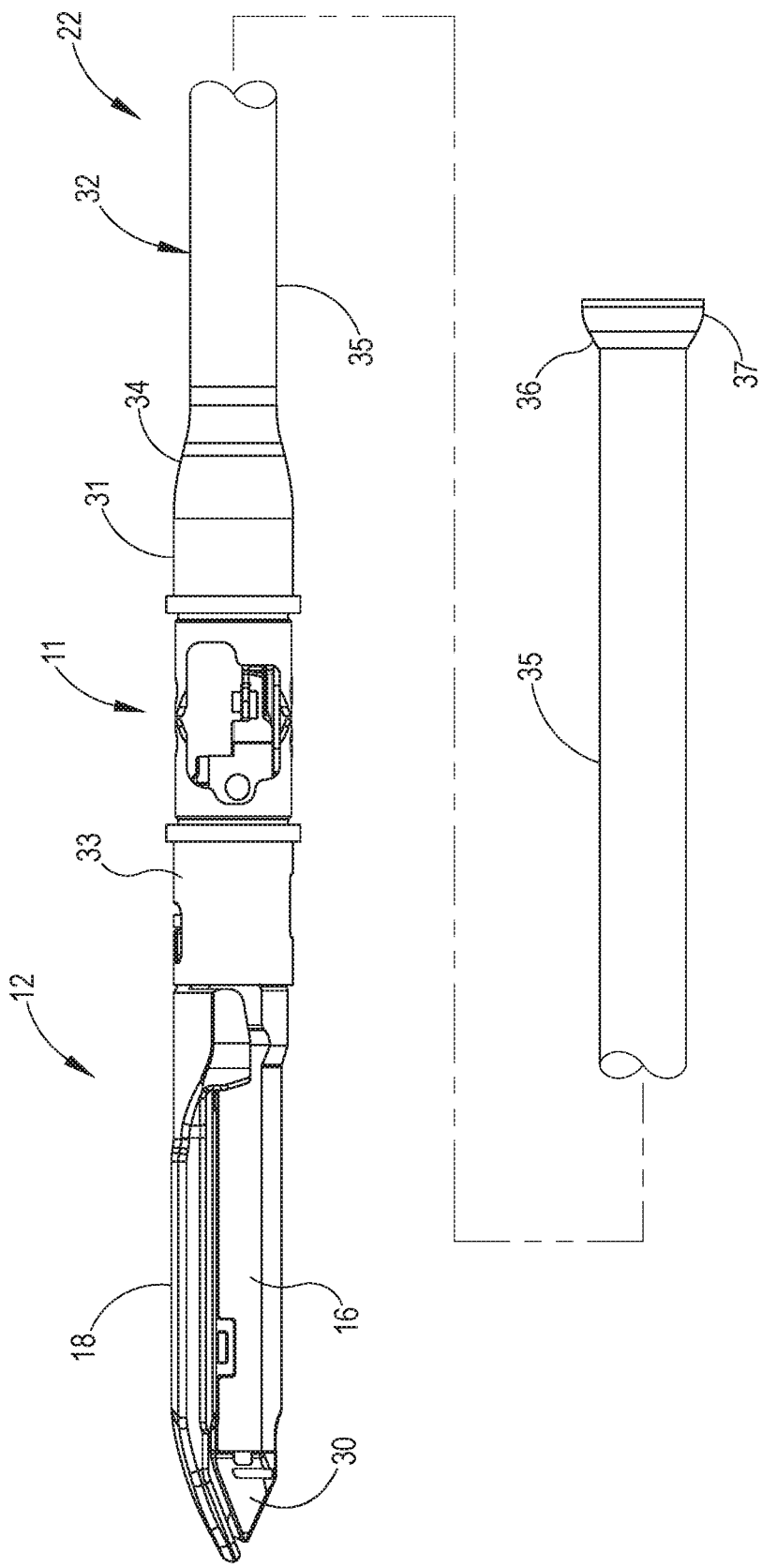
FIG. 2 depicts a side view of a shaft and an end effector of the instrument of FIG. 1.

FIG. 2 shows shaft (22) comprising a closure tube (32) that may be driven distally by pivoting closure trigger (26) toward pistol grip (24). Closure tube (32) is coupled with closure ring (33), such that closure ring (33) translates distally when closure tube (32) translates distally. Closure ring (33) then drives anvil (18) to pivot toward lower jaw (16) when closure ring (33) translates distally, to thereby clamp tissue positioned between jaws (16, 18).

Closure tube (32) has portions (31, 34, 35, 36, 37) with varying diameters. Distal portion (31) is positioned distal on closure tube (32) and is sized to couple to articulation joint (11). Ramped distal portion (34) is connected with and proximal to distal portion (31). Ramped distal portion (34) has a diameter that gradually decreases in the proximal direction. Central portion (35) is proximally connected with ramped distal portion (34). Central portion (35) of closure tube (32) has a substantially constant diameter that is smaller than the diameter of distal portion (31) and is configured to be positioned within a thoracotomy (i.e., between a pair of ribs), within a trocar, etc. The decreased diameter of central portion (35) of closure tube (32) allows for increased range of movement and positioning of end effector (12) without prying ribs or otherwise damaging soft tissue around the thoracotomy. The transition between the diameters of distal portion (31) and central portion (35) provided by ramped distal portion (34) may reduce patient trauma and prevent seal inversion if instrument (10) is used with a trocar.

Ramped proximal portion (36) is proximally connected with central portion (35) of closure tube (32) and has a diameter that gradually increases in the proximal direction. Proximal portion (37) of closure tube (32) is proximally connected with ramped proximal portion (36) and is sized to couple with distal portion (38) of handle portion (20). Proximal portion (37) has a larger diameter than central portion (35). Portions (31, 34, 35, 36, 37) of closure tube (32) may be formed from a single piece or multiple pieces of shaft (22). Shaft (22) may be manufactured by manual expansion, hydroforming, tube welding, or other suitable processes apparent to one with ordinary skill in the art in view of the teachings herein.

FIGS. 3A-3B show the coupling of closure ring (33) and distal portion (31) of closure tube (32) using one or more closure links (50) with other components omitted for clarity. As shown, each closure link (50) includes proximal and distal pins (52, 54) extending from a body (56) of closure link (50). Proximal end (58) of body (56) extends proximally of proximal pins (52). Similarly, distal end (60) of body (56) extends proximally of distal pins (54). In other words, proximal and distal pins (52, 54) are disposed on the inside of body (56) and surrounded by body (56). Closure links (50) include first and second opposing sides (62, 64). Distal portion (31) of closure tube (32) includes first and second arms (66) that include first and second apertures (68) configured to receive proximal pins (52) of respective closure links (50). Similarly, closure ring (33) includes first and second arms (70) that respectively include first and second apertures (72) configured to receive distal pins (54) of closure links (50).

Figure 4A:
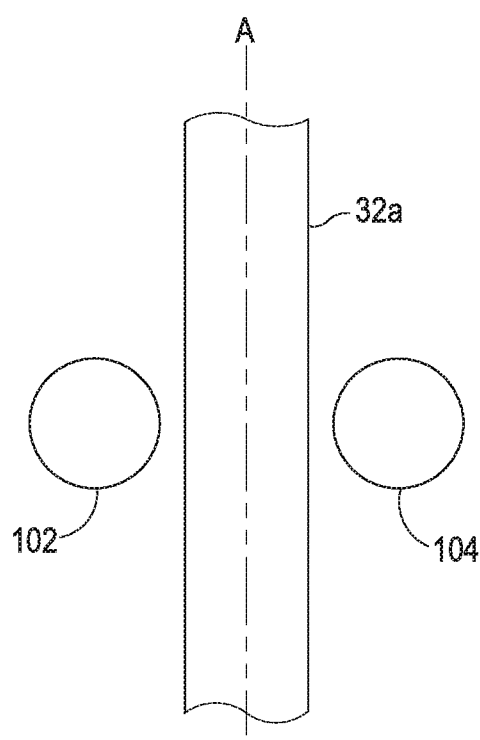
FIG. 4A depicts a schematic view of a shaft having a uniform cross-section inserted between two ribs.
Figure 4B:
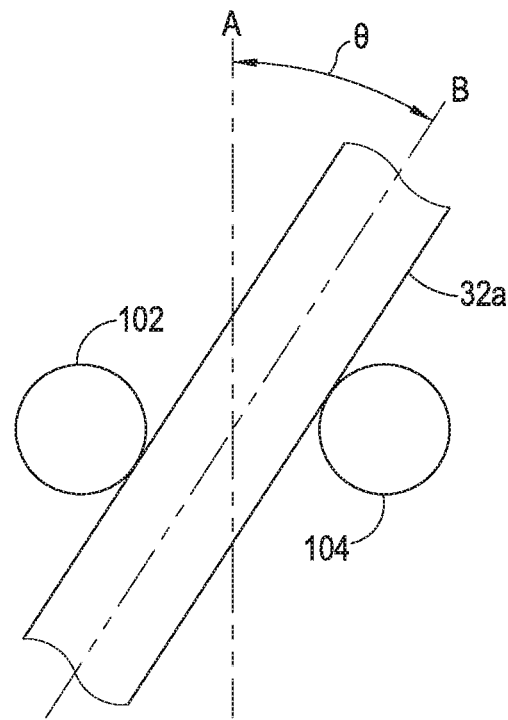
FIG. 4B depicts a schematic view of the shaft of FIG. 4A having a uniform cross-section pivoted between two ribs.

FIGS. 4A-4B show a closure tube (32a) having a uniform cross-sectional area along its entire length. Closure tube (32a) functions similarly to closure tube (32) described above with reference to FIGS. 1-3B, except that closure tube (32a) has uniform cross-sectional area along its entire length. As shown in FIG. 4A, closure tube (32a) is inserted between a pair of ribs (102, 104). Closure tube (32a) defines a longitudinal axis (A) that is perpendicular to ribs (102, 104) at insertion. Closure tube (32a) is then angled to position end effector (not shown) within the patient. As shown in FIG. 4B, closure tube (32a) is angled until closure tube (32) contacts each rib (102, 104). Closure tube (32a) defines a longitudinal axis (B) in this position. The angle between longitudinal axis (A) and longitudinal axis (B) is the maximum pivot angle ($\theta$) that closure tube (32a) may travel to position end effector (12) until closure tube (32a) contacts ribs (102, 104).

Figure 5A:
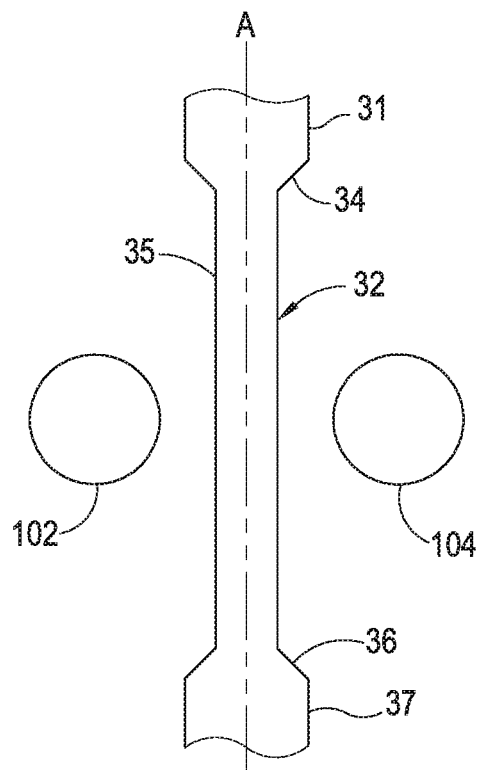
FIG. 5A depicts a schematic view of the shaft of the instrument of FIG. 1 inserted between two ribs.
Figure 5B:
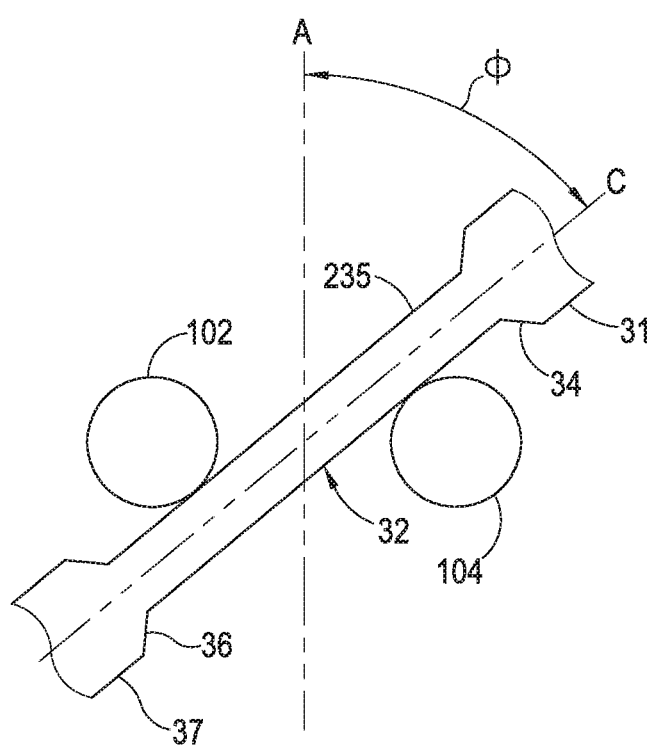
FIG. 5B depicts a schematic view of the shaft of the instrument of FIG. 1 pivoted between two ribs.

FIGS. 5A-5B show central portion (35) of closure tube (32) of shaft (22) positioned between ribs (102, 104). Shaft (22) may be positioned within a thoracotomy (i.e., between a pair of ribs), a trocar, etc. to increase movement and positioning of end effector (12) as compared to movement and positioning permitted by shaft (32a) having a uniform cross-sectional area along its entire length, as shown and described with reference to FIGS. 4A-4B. Closure tube (32) is inserted perpendicularly between ribs (102, 104) at the same longitudinal axis (A) as closure tube (32a). Closure tube (32) is then pivoted to position end effector (12) until closure tube (32) contacts ribs (102, 104). Closure tube (32) defines longitudinal axis (C) at this position. The angle between longitudinal axis (A) and longitudinal axis (C) is the maximum pivot angle ($\phi$) that closure tube (32) may travel. Because central portion (35) of closure tube (32) has a smaller diameter than closure tube (32a) having a uniform cross-section along its entire length, closure tube (32) has a greater maximum pivot angle ($\phi$) than the maximum pivot angle ($\theta$) of closure tube (32a). This beneficially enables closure tube (32) to increase the range of movement and positioning of end effector (12).

C. Exemplary Articulation Joint

As described above with reference to FIG. 1 and below with reference to FIGS. 6A-6B, shaft (22) distally terminates in an articulation joint (11), which is further coupled to end effector (12). Articulation joint (11) may be remotely articulated by control knob (39) such that end effector (12) may be deflected from the longitudinal axis (LA) of shaft (22). End effector (12) may reach behind an organ or approach tissue from a desired angle or for other reasons. Articulation joint (11) may enables deflection of end effector (12) along a single plane or multiple planes. By way of example only, some merely illustrative alternative examples of articulation joint (11) and control knob (39) are disclosed in U.S. Pat. No. 9,186,142, issued on Nov. 17, 2015, the disclosure of which is incorporated by reference herein.

Figure 6A:
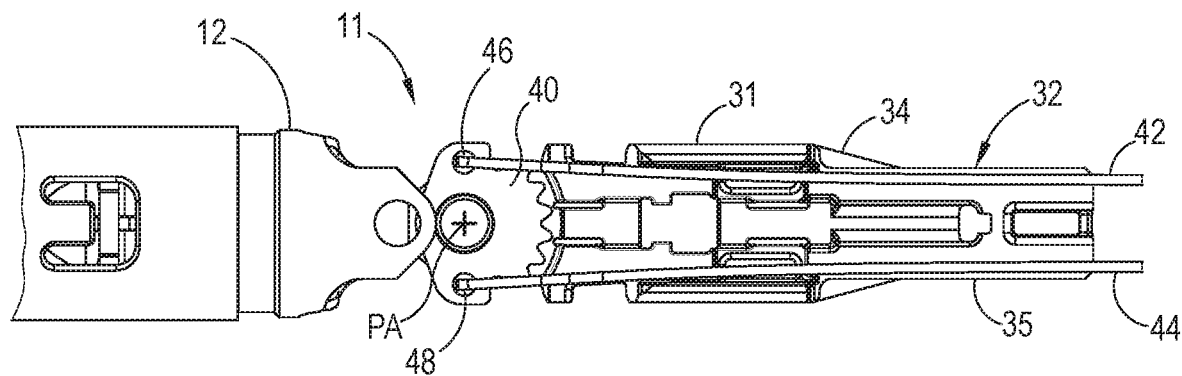
FIG. 6A depicts a cross-sectional top view of an articulation joint of the instrument of FIG. 1 in a non-articulated configuration.
Figure 6B:
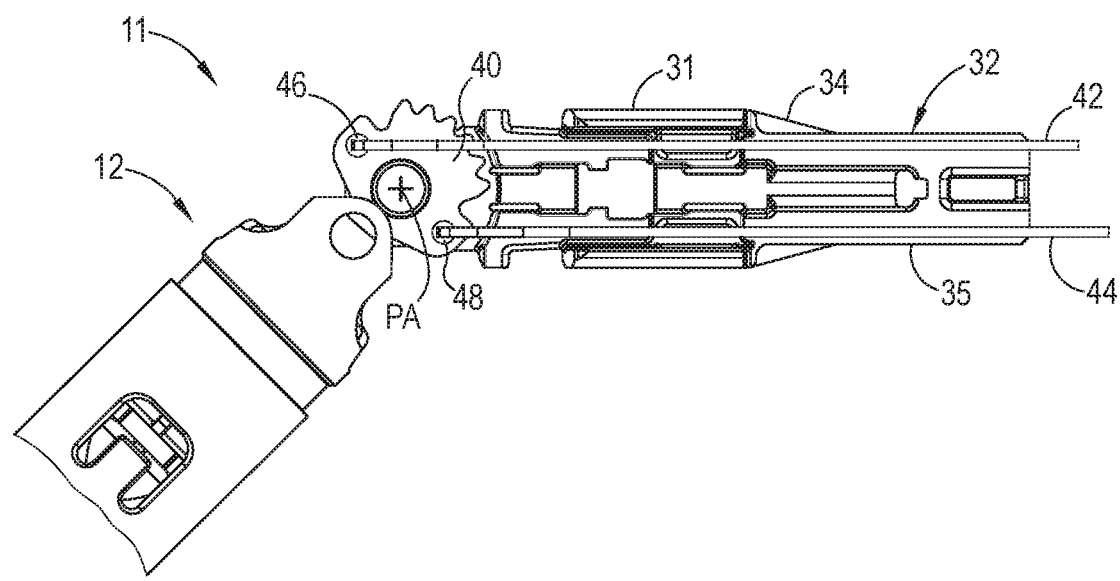
FIG. 6B depicts a cross-sectional top view of the articulation joint of FIG. 6A in an articulated configuration.

FIGS. 6A-6B show articulation joint (11) of the present example in greater detail, with several components of articulation joint (11) being omitted. Such omitted components may be configured and operable in accordance with at least some of the teachings of U.S. Pat. No. 9,186,142, issued on Nov. 17, 2015, the disclosure of which is incorporated by reference herein. FIG. 6A shows articulation joint (11) and end effector (12) in a nonarticulated position such that end effector (12) is longitudinally aligned with shaft (22). Articulation joint (11) comprises an articulation gear (40) and articulation bands (42, 44). Gear (40) is coupled with the distal end of closure tube (32) of shaft (22). Gear (40) is configured to rotate about pivot axis (PA) to position end effector (12) at the desired articulation angle. Articulation bands (42, 44) travel the length of shaft (22) such that the proximal ends of bands (42, 44) couple to control knob (39). The distal end of bands (42, 44) couple to gear (40) through openings (46, 48) on each side of gear (40). As shown, band (42) is coupled with opening (46) and band (44) is coupled with opening (48).

FIG. 6B shows articulation joint (11) and end effector (12) in an articulated position such that end effector (12) is deflected at an oblique angle relative to the longitudinal axis of shaft (22). To articulate end effector (12), control knob (39) is rotated. As shown, gear (40) is rotated counterclockwise such that opening (46) translated distally, while opening (48) translated proximally. The translation of openings (46, 48) cause bands (42, 44) to flare inwardly in the lateral direction. The teeth of gear (40) may selectively engage a locking member to provide selective locking of articulation angle. By way of example only, some merely illustrative alternative examples of locking members are disclosed in U.S. Pat. No. 9,186,142, issued on Nov. 17, 2015, and U.S.

Pat. No. 9,867,615, issued on Jan. 16, 2018, the disclosures of which are incorporated by reference herein.

D. Exemplary Operation

In an exemplary use, instrument (10) may be inserted to a surgical site in a nonarticulated state with jaws (16, 18) of end effector (12) in the closed position. In the nonarticulated state, end effector (12) is longitudinally aligned with shaft (22), as shown in FIG. 6A. When instrument (10) is inserted to the surgical site, articulation joint (11) and end effector (12) may be inserted through the cannula passageway of a trocar, or through a thoracotomy, to position central portion (35) of closure tube (32) within the passageway or thoracotomy. Once closure tube (32) is positioned, closure tube (32) may be pivoted to position end effector (12). For instance, closure tube (32) may be pivoted to a desired pivot angle ($\phi$), as shown in FIGS. 5A-5B. Rotation knob (13) may be actuated to rotate end effector (12) relative to handle portion (20) to orient jaws (16, 18) at a desired angular orientation about the longitudinal axis of shaft (22).

To actuate articulation joint (11), control knob (39) may be actuated. The rotation of control knob (39) is converted to opposing longitudinal translation of bands (42, 44). Bands (42, 44) then rotate gear (40) of articulation joint (11), as shown in FIG. 6B, to pivot end effector (12). Once end effector (12) is articulated to a desired location, closure trigger (26) may then be actuated toward pistol grip (24) to cause the closing of anvil (18) toward lower jaw (16). Such closing of anvil (18) is provided through closure tube (32) and closure ring (33), which longitudinally translate relative to handle portion (20) in response to pivoting of closure trigger (26) relative to pistol grip (24). Once end effector (12) is closed, the tissue captured between anvil (18) and lower jaw (16) may be cut and stapled by actuating firing trigger (28).

To open end effector (12), closure trigger (26) may be released away from pistol grip (24) to translate closure tube (32) and closure ring (33) proximally and pivot anvil (18) away from lower jaw (16). End effector (12) may then be returned to the nonarticulated position. Control knob (39) may be rotated to longitudinally align end effector (12) with shaft (22), as shown in FIG. 6A. With instrument (10) in the nonarticulated position and end effector jaws (16, 18) in the open position, staple cartridge (30) may be replaced with a new staple cartridge such that instrument (10) may cut and/or staple additional tissue. Alternatively, closure trigger (26) may again be actuated to close jaws (16, 18) of end effector (12).

Instrument (10) may otherwise be configured and operable in accordance with any of the teachings of any of the patent references cited herein. Additional exemplary modifications that may be provided for instrument (10) will be described in greater detail below. The below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. EXEMPLARY CLOSURE TUBE AND METHODS OF MANUFACTURE

As described above, closure tube (32) of instrument (10) may be formed from welding one or more pieces of shaft together using manual expansion, hydroforming, tube welding, or other suitable processes. However, it may be desirable to form closure tube (32) from two or more different materials. For example, proximal and distal portions may desirably be formed from a polymeric material, while a central portion may desirably be formed from a metallic material. Alternatively, the proximal portion may desirably be formed from a polymeric material, while the central and distal portions may desirably be formed from a metallic material. Additionally, it may be desirable to manufacture closure tube (32) in a low-cost manner. Moreover, it may be desirable to strengthen the coupling between the pieces comprising closure tube (32) and/or selective couple the multiple piece together when desired.

It may therefore be desirable to manufacture an exemplary closure tube (210) that addresses these and other shortcomings, while also enabling closure tube (210) to function interchangeably with closure tube (32) described above described above with reference to FIGS. 1-3B and FIGS. 5A-6B. More specifically, similar to the operation of instrument (10), where driving closure tube (32) distally translates closure ring (33) distally, causing anvil (18) to pivot toward lower jaw (16), driving closure tube (210) distally also translates closure ring (33) distally, causing anvil (18) to pivot toward lower jaw (16). Additional details of closure tube (210) are described below with reference to the following figures.

A. Exemplary Closure Tube

Figure 7:
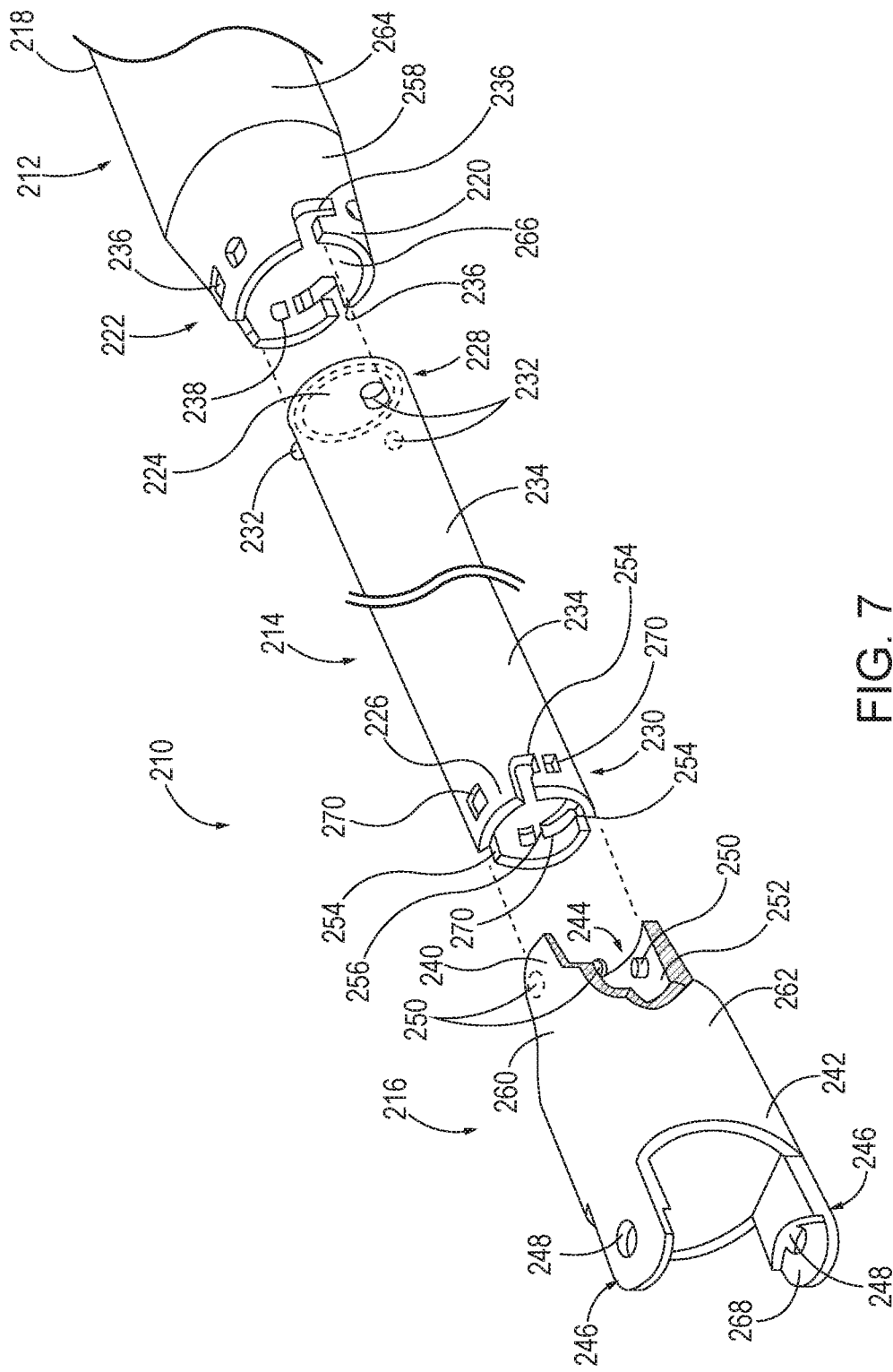
FIG. 7 depicts an exploded view of an exemplary closure tube that may be incorporated into the instrument of FIG. 1, with the closure tube including a proximal coupler, a tube, and a distal coupler.

FIG. 7 shows an exploded view of an exemplary closure tube (210) that includes a proximal coupler (212), a tube (214), and a distal coupler (216). As shown, proximal coupler (212), tube (214), and distal coupler (216) are formed as entirely separate components. Closure tube (210) is intended to extend proximally from opposing jaws (16, 18) of end effector (12). Proximal coupler (212) has proximal and distal ends (218, 220). Proximal coupler (212) is formed from a polymeric material. Proximal coupler (212) includes a distal coupling feature (222) adjacent distal end (220), shown in the form of a receiver portion of a bayonet coupling feature. Similarly, tube (214) has proximal and distal ends (224, 226) and is formed of a metallic material. As will be described in greater detail with reference to an exemplary method (410) of FIG. 15, tube (214) may be formed from a rolled metallic sheet and welded at the seam to form a tubular structural shape. As shown, tube (214) includes proximal and distal coupling features (228, 230) in the form of opposing insertion and receiver portions of bayonet coupling features. Proximal coupling feature (228) is disposed adjacent proximal end (224) of tube (214) and is configured to engage distal coupling feature (222) of proximal coupler (212) to securably lock tube (214) and proximal coupler (212) together. Distal coupling feature (230) of tube (214) is disposed adjacent distal end (226) of tube (214) and engages distal coupler (216).

As shown in FIG. 7, proximal coupling feature (228) of tube (214) includes projections (232) formed on an outer surface (234) of tube (214) that are configured to lockingly engage channels (236) of distal coupling feature (222) of proximal coupler (212). As shown, three projections (232) are circumferentially spaced around the perimeter of tube (214); however, more or fewer projections (232) having the same or varying spacing are also envisioned. Likewise, three channels (236) are circumferentially spaced around the perimeter of proximal coupler (212) and correspondingly receive projections (232). More or fewer channels (236) having the same or varying spacing are also envisioned.

As shown in FIG. 7 and in greater detail in FIG. 8-10C, channels (236) include ramps (238) that are configured guide projections (232) from an unlocked configuration to a locked configuration. Once in the locked configuration shown in FIG. 10C, ramps (238) prevent projections (232) from decoupling, such that tube (214) and proximal coupler (212) remain securely locked together. While proximal coupling feature (228) of tube (214) is shown to include projections (232) and distal coupling feature (222) of proximal coupler (212) is shown to include channels (236), it is also envisioned that this relationship may be reversed, such that proximal coupling feature (228) of tube (214) includes at least one channel (236) and distal coupling feature (222) of proximal coupler (212) includes at least one projection (232). It is also envisioned that proximal coupling feature (228) of tube (214) may include at least one projection (232) and at least one channel (236), and distal coupling feature (222) of proximal coupler (212) may include at least one corresponding channel (236) and at least one at least one corresponding projection (232). Distal coupling feature (222) of proximal coupler (212) and/or proximal coupling feature (228) of tube (214) may include one or more snap fit features in addition to, or in lieu of, the described bayonet features.

Distal coupler (216) has proximal and distal ends (240, 242). Distal coupler (216) is formed from a polymeric or metallic material. Distal coupler (216) includes a proximal coupling feature (244) disposed adjacent proximal end (240) of distal coupler (216). Proximal coupling feature (244) of distal coupler (216) is configured to engage distal coupling feature (230) of tube (214) to securably lock distal coupler (216) and tube (214) together, similar to the engagement of distal coupling feature (222) of proximal coupler (212) and proximal coupling feature (228) of tube (214) shown in FIGS. 8-10C. Distal coupler (216) further includes arms (246), which include respective apertures (248), projecting from distal end (242) of distal coupler (216) as will be described with reference to FIGS. 11-12.

Regarding the coupling of tube (214) and distal coupler (216), distal coupling feature (222) of tube (214) and proximal coupling feature (228) of distal coupler (216) include one or more snap fit features (not shown) and/or one or more bayonet coupling features. As shown, proximal coupling feature (228) includes projections (250) formed on an inner surface (252) of distal coupler (216) that are configured to lockingly engage channels (254) of distal coupling feature (230) of tube (214). As shown, three projections (250) are circumferentially spaced around the perimeter of distal coupler (216); however, more or fewer projections (250) having varying spacings are also envisioned. Likewise, three channels (254) are circumferentially spaced around the perimeter of tube (214). As shown, proximal end (240) of distal coupler (216) circumferentially overlies at least a portion of distal coupling feature (230) of tube (214). More or fewer channels (254) having varying spacings are also envisioned. Channels (254) include ramps (256) that are configured guide projections (250) from the unlocked configuration to the locked configuration. Once in the locked configuration, ramps (256) prevent projections (250) from uncoupling once rotated past ramp (256), such that tube (214) and distal coupler (216) remain securely locked together once projection (250) is situated within locking portion (270) of channel (254).

With continued reference to FIG. 7, proximal coupler (212), tube (214), and distal coupler (216) have tubular shapes with hollow interiors. While round tubular shapes are shown, other tubular shapes are also envisioned (e.g. square, rectangular etc.). Additionally, as shown, proximal coupler (212) includes a narrowing region (258) adjacent distal end (220), and distal coupler (216) includes a narrowing region (260) adjacent proximal end (240). As such, the average diameter of proximal coupler (212) is greater than average diameter of tube (214). Likewise, the average diameter of distal coupler (216) is greater than average diameter of tube (214). As a result, closure tube (210) including proximal coupler (212), tube (214) and distal coupler (216) have increased angular reach similar to closure tube (32) shown and described with reference to FIGS. 5A-5B. This contrasts a uniform diameter closure tube (32a) shown and described with reference to FIGS. 4A-4B having a more limited reach between ribs (102, 104). Additionally, an outer surface (262) of distal coupler (216) is generally smooth and continuous which is configured to prevent outer surface (262) from snagging or catching on tissue. Moreover, closure tube (210) including proximal coupler (212), tube (214) and distal coupler (216) have a generally smooth and continuous exterior.

Figure 8:
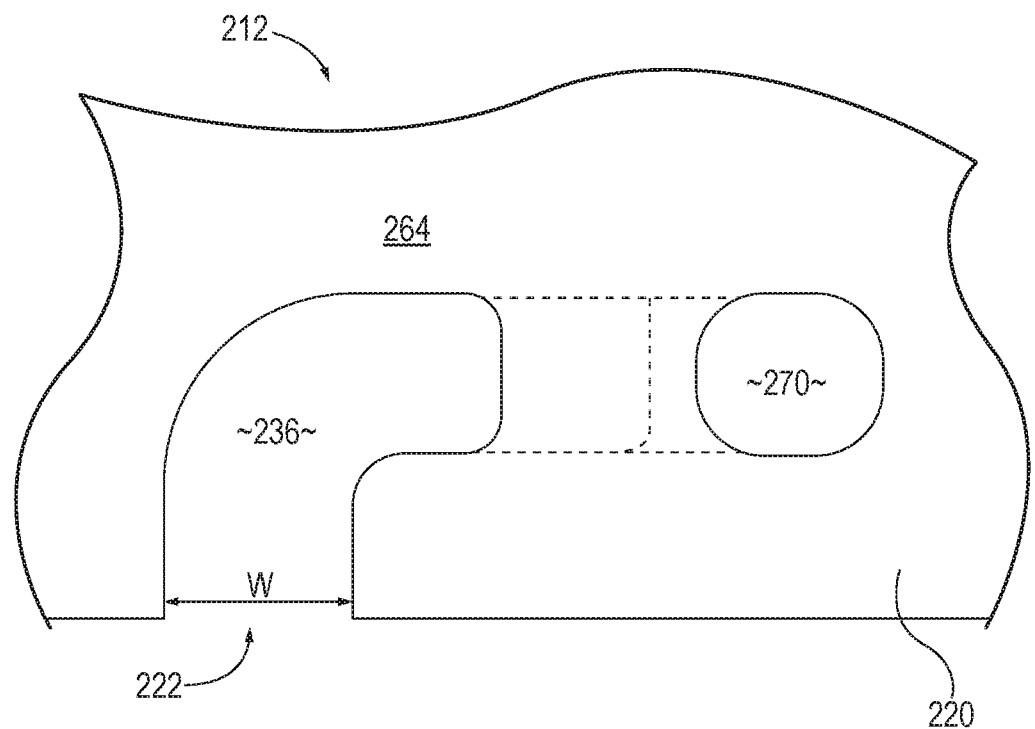
FIG. 8 depicts an enlarged portion of an outer surface of a distal coupling feature of the proximal coupler of FIG. 7.
Figure 9:
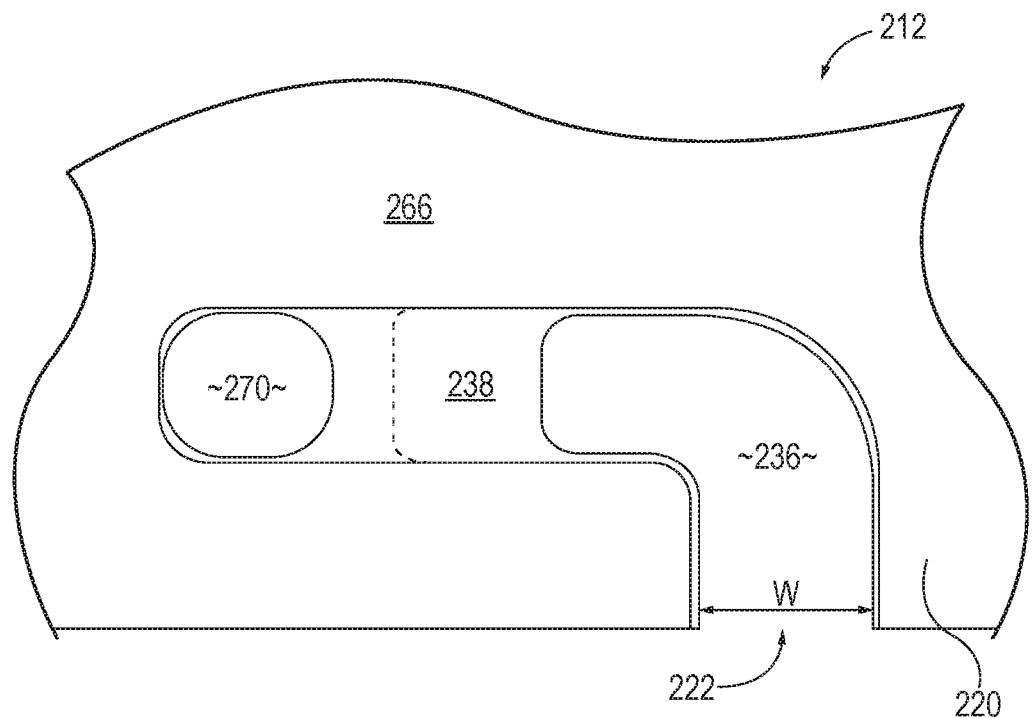
FIG. 9 depicts an enlarged portion of an inner surface of the distal coupling feature of the proximal coupler of FIG. 7.

FIG. 8 shows an enlarged portion of an outer surface (264) of distal coupling feature (222) of proximal coupler (212), while FIG. 9 shows an enlarged portion of an inner surface (266) of distal coupling feature (222) of proximal coupler (212). In FIGS. 8-9, the outer and inner surfaces (264, 266) are shown as being flat for greater clarity, however, outer and inner surfaces (264, 266) are curved, as shown in FIG. 7. As shown in FIGS. 8-9, ramp (238) of channel (236) is configured move projection (232) from an unlocked configuration to a locked configuration. Ramp (238) prevents projection from unlocking once rotated past ramp (238) and situated within locking portion (270) of channel (236). Ramp (238) spans across entire width (W) of channel. The features described in FIGS. 8-9 pertaining to distal coupling feature (222) of proximal coupler (212) also apply equally to distal coupling feature (230) of tube (214). Instead of or in addition to ramp (238, 256), channel (236, 254) may have a tortuous path preventing projection (232, 250) from unlocking.

Figure 10A:
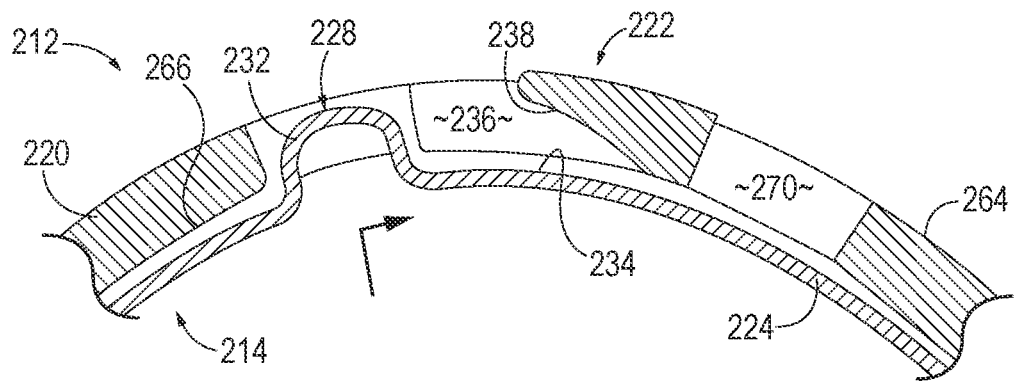
FIG. 10A depicts a cross-sectional view of a proximal coupling feature of the tube of FIG. 7 being inserted into the distal coupling feature of the proximal coupler of FIG. 7.
Figure 10B:
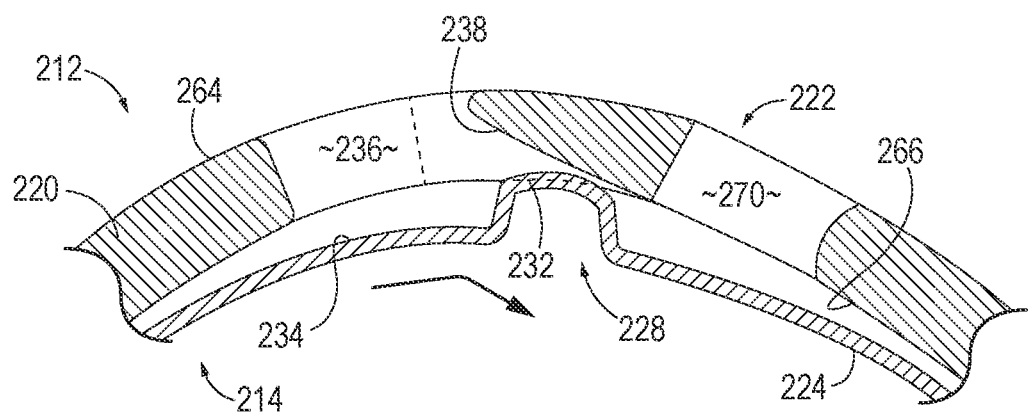
FIG. 10B depicts a cross-sectional view of the proximal coupling feature of the tube of FIG. 7 being rotated to slidably engage a ramp of the distal coupling feature of the proximal coupler of FIG. 7.
Figure 10C:
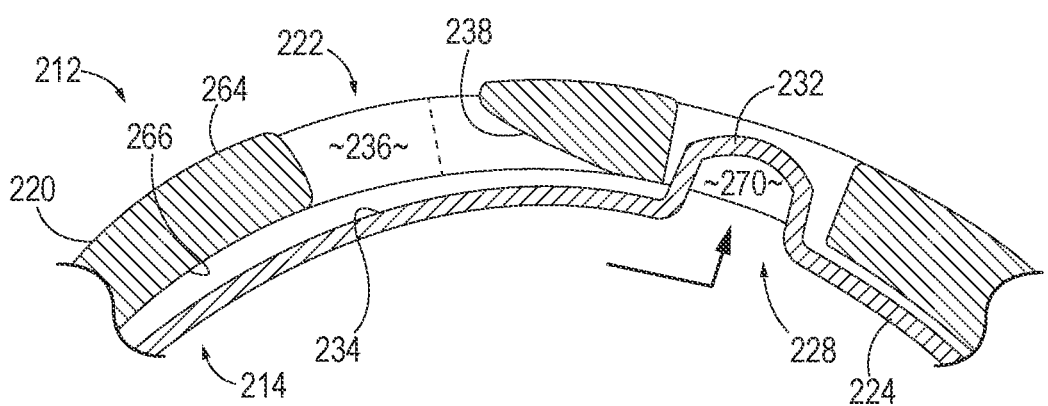
FIG. 10C depicts a cross-sectional view of the proximal coupling feature of the tube of FIG. 7 after being fully rotated relative to the distal coupling feature of the proximal coupler of FIG. 7.

FIGS. 10A-10C show sectional views of the coupling of proximal coupler (212) and tube (214). More specifically, FIG. 10A shows projection (232) of tube (214) being inserted into channel (236) of proximal coupler (212). Once projection (232) is inserted into channel (236), tube (214) is rotated relative to proximal coupler (212) as shown in FIG. 10B, such that projection (232) of tube (214) slidably engages ramp (238) of proximal coupler (212). Ramp (238) is shown in the sectional views of FIGS. 10A-10C as a right triangular structure with a curvilinear outside surface (264). While ramp (238) is shown as planar, ramp (238) may also be curved if desired. Tube (214) is further rotated until projection (232) fully engaged with locking portion (270) of channel (236) as shown in FIG. 10C. While tube (214) is described as being rotated relative to proximal coupler (212), it is envisioned that proximal coupler (212) be rotated relative to tube (214). As shown, the thickness of tube (214) is less than the thickness of proximal coupler (212).

B. Exemplary Closure Link

Figure 11:
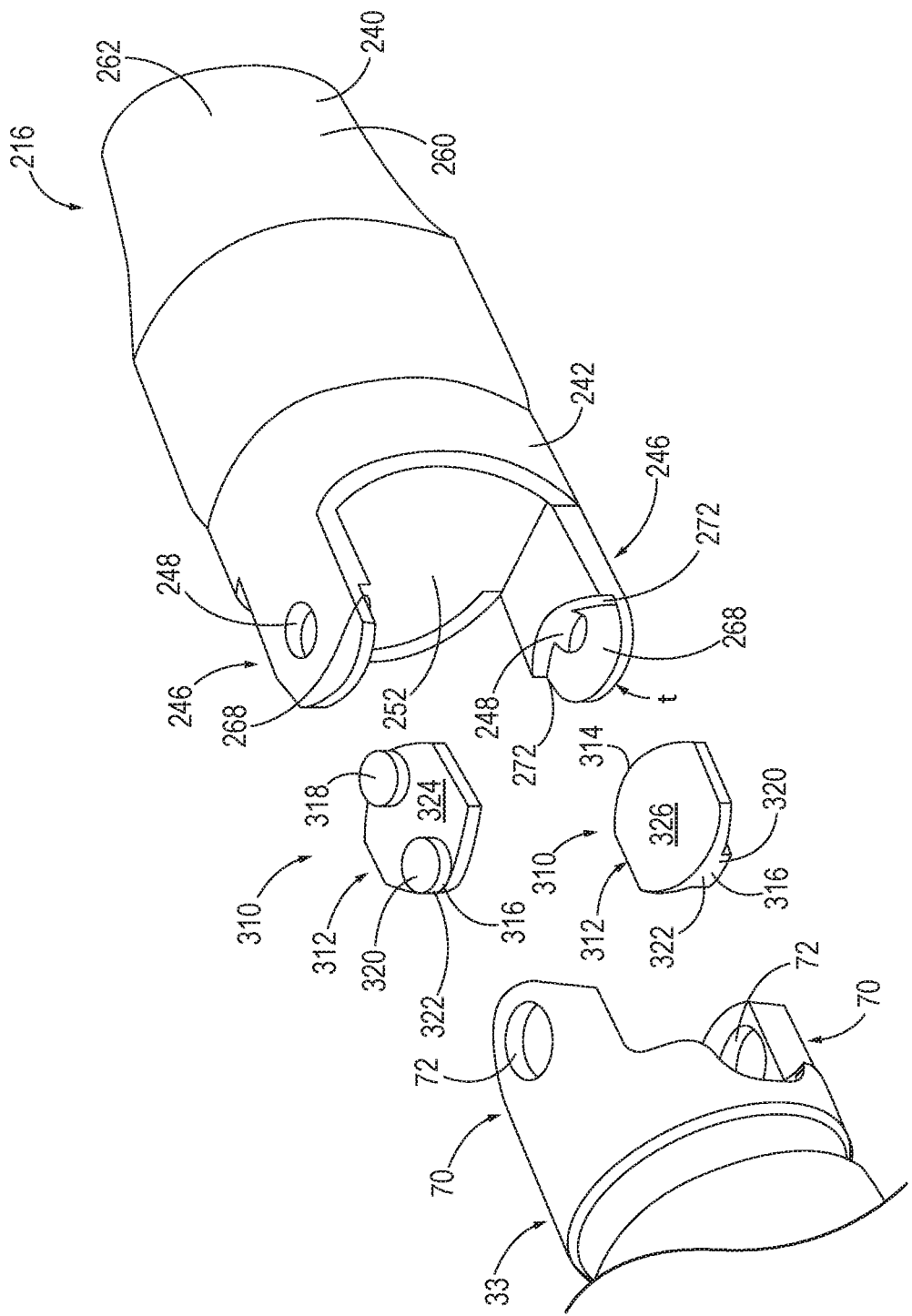
FIG. 11 depicts an exploded perspective view of the closure tube of FIG. 7 being coupled with the closure ring of FIG. 3A using exemplary closure links.

As shown in FIGS. 11-14, instrument includes at least one closure link (310) configured to rotatably couple distal coupler (216) and end effector (12). As shown in FIG. 11, each closure link (310) includes a body portion (312) having a proximal most end (314) and a distal most end (316). Closure links (310) include a proximal pin (318) and a distal pin (320). Proximal and distal pins (318, 320) each extend from a first surface (324) of body portion (312) which is opposite a second surface (326) of body portion (312). Proximal pin (318) is disposed at proximal most end (314a) of body portion (312) and is configured to be received within aperture (248) of distal coupler (216). Distal pin (320) is disposed at distal most end (316) of body portion (312) and is configured to be received within aperture (72) of coupling ring (33). Outer surfaces (322) of proximal and distal pins (318, 320) define the length of body portion (312) between proximal and distal most ends (314, 316) of closure link (310). As previously described with reference to FIG. 7 and shown in FIG. 11, distal coupler (216) includes arms (246) projecting from distal end (242) of distal coupler (216). Arms (246) include apertures (248) adjacent respective cutout portions (268).

Figure 12:
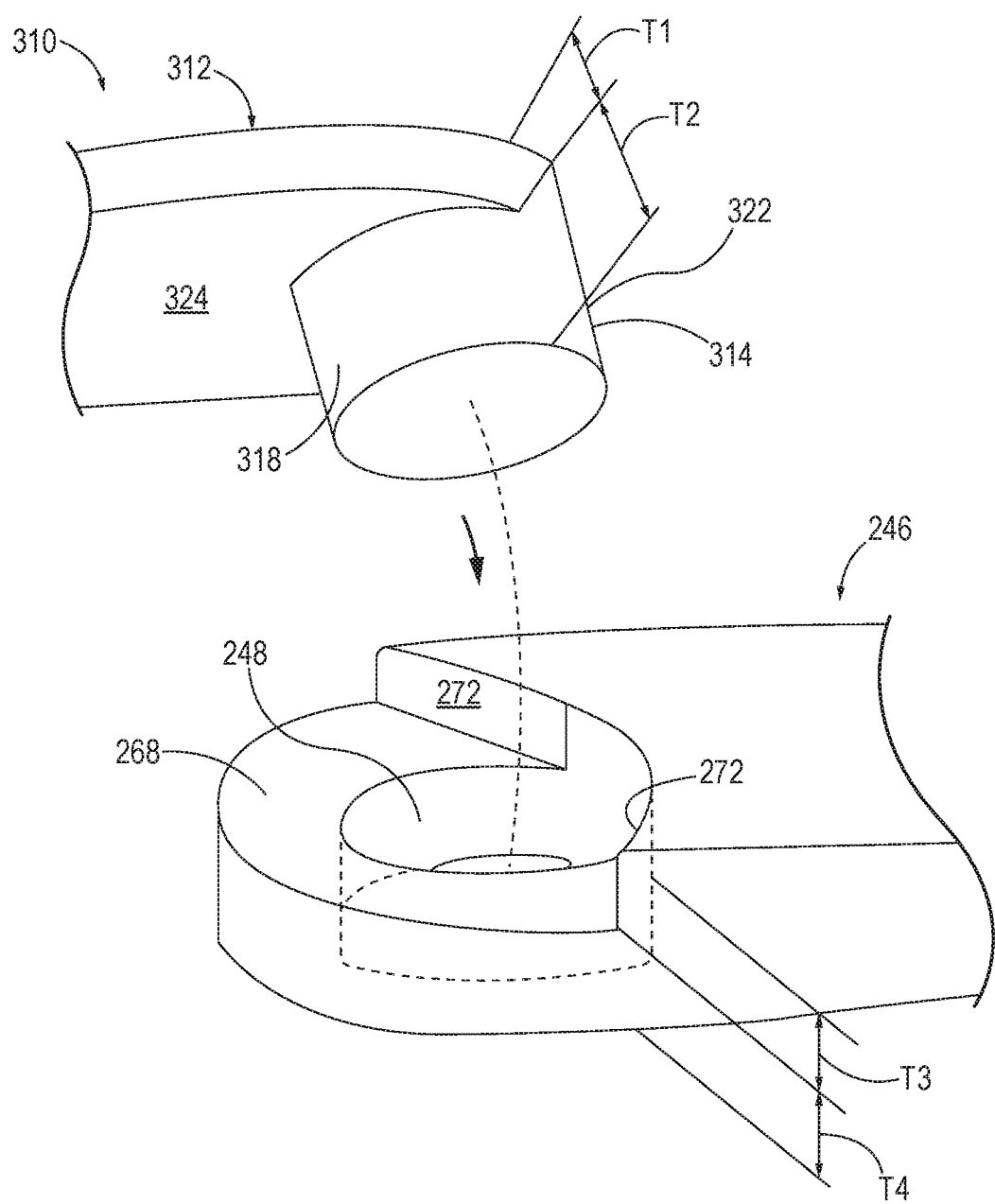
FIG. 12 depicts an enlarged perspective view of the closure link of FIG. 11 being inserted into the closure tube of FIG. 11.

FIG. 12 shows an enlarged perspective view of closure link (310) being inserted into aperture (248) of distal coupler (216) of closure tube (210). For example, according to the example shown, body portion (312) has a thickness (T1) of about 0.020 inches which may be the same or similar to a thickness (T3) of about 0.020 inches of cutout portion (268). Similarly, proximal and distal pins (318, 320) may have a thickness (T2) of about 0.045 inches which may be the same or similar to a thickness (T4) of about 0.045 inches of the remaining thickness of cutout portion (268). These dimensions are described for exemplary purposes and are not intended to be limiting. As shown, cutout wall (272) of cutout portion (268) has a similar curvilinear shape to curved proximal side (328) of body portion (312). This may prohibit some degree of rotational movement of closure link (310) relative to distal coupler (216) of closure tube (210).

Figure 13A:
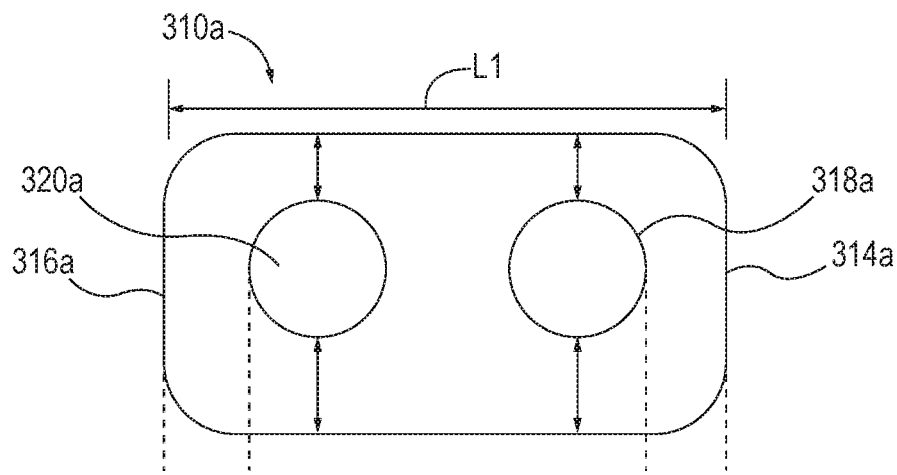
FIG. 13A depicts the closure link of FIG. 11 prior to undergoing a manufacturing process.
Figure 13B:
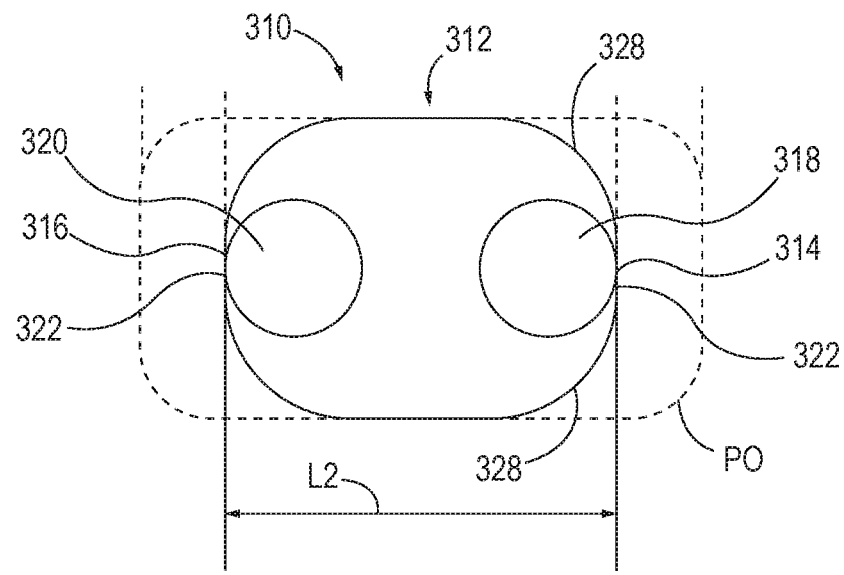
FIG. 13B depicts the closure link of FIG. 13A after undergoing a manufacturing process.
Figure 14:
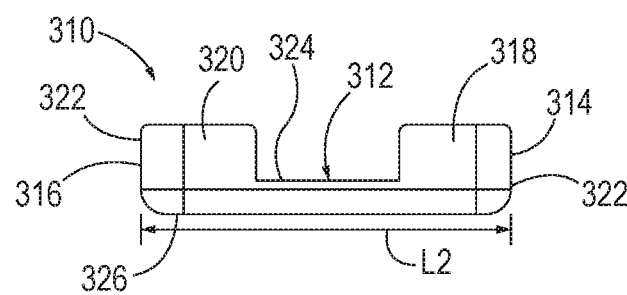
FIG. 14 depicts a side view of the closure link of FIG. 13B.

FIG. 13A shows a closure link (310a) prior to being subjected to at least one manufacturing process to remove material at each of proximal and distal most ends (314a, 316a) of body portion (312a). FIGS. 13B and 14 show closure link (310) after being subjected to at least one manufacturing process, with a prior outline (PO) of closure link (310a) being shown in phantom. It is envisioned that at least one manufacturing process may include, for example, stamping or machining among other subtractive manufacturing processes. As shown, material is removed from proximal and distal pins (318a, 320a) to form proximal and distal pins (318, 320). As shown in FIG. 13A, closure link (310a) has a length (L1) of 0.475 inches. After at least one manufacturing process, closure link (310) has a length (L2) of about 0.350 inches as shown in FIGS. 13B and 14. These dimensions are shown and described for exemplary purposes and are not intended to be limiting.

C. Exemplary Method of Manufacture

Figure 15:
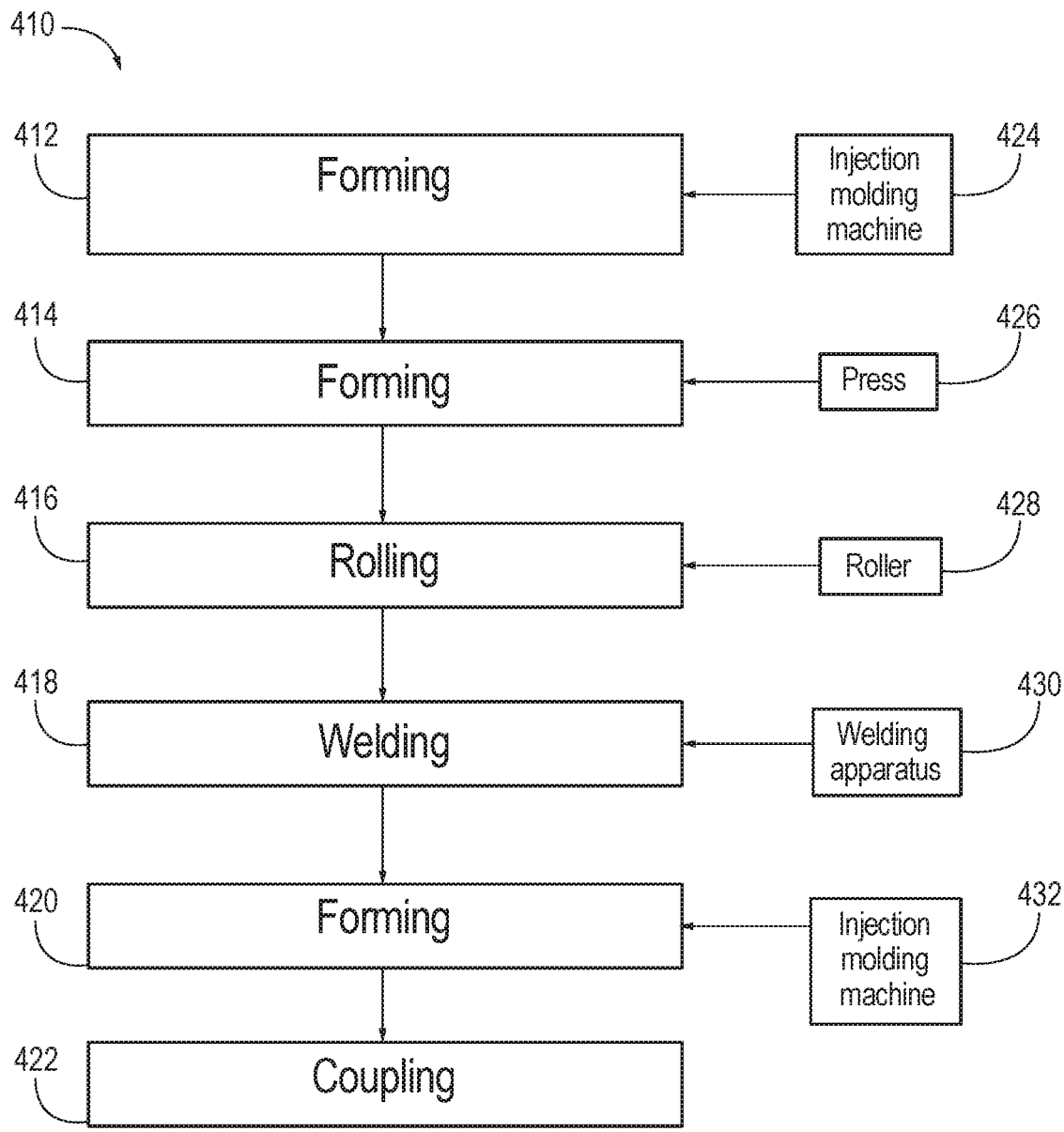
FIG. 15 depicts an exemplary method of manufacturing the closure tube of FIG. 7 that may be incorporated into the instrument of FIG. 1.

FIG. 15 shows an exemplary method (410) of manufacturing closure tube (210) of FIG. 7, which is configured to be used in lieu of closure tube (32) of surgical instrument (10). As shown, method (410) includes steps (412, 414, 416, 418, 420, 422). As previously described with respect to FIGS. 7-12, closure tube (210) includes proximal coupler (212), tube (214), and distal coupler (216).

At step (412), method (410) includes forming proximal coupler (212) from a polymeric material using an injection molding machine (424). Proximal coupler (212) includes coupling feature (222). At step (414), method (410) includes forming at least one coupling feature (228, 230) into the metallic sheet. For example, coupling feature (228, 230) may be stamped into metallic sheet using a press (426); however, a variety of other manufacturing processes may also be suitably used to impart coupling feature (228, 230).

At step (416), method (410) includes rolling the metallic sheet to form a metallic tubular structure using a roller (428). At step (418), method (410) includes welding the metallic tubular structure to form tube (214) of surgical instrument (10) using a welding apparatus (430). For example, ends of tubular structure may be welded using a butt joint or a lap joint. At step (420), method (410) includes forming distal coupler (216) of surgical instrument (10) using a metal injection molding machine or a plastic injection molding machine (432). Distal coupler (216) includes at least one coupling feature (244). Coupling feature (244) may be imparted during the molding process or may be formed after the molding process.

At step (422), method (410) includes coupling proximal coupler (212) to tube (214) and distal coupler (216) to the tube (214) using the coupling features (222, 228, 230, 244) of proximal coupler (212), tube (214), and distal coupler (216). Proximal coupler (212) may be coupled to tube (214) before, simultaneously with, or after tube (214) is coupled with distal coupler (216). As previously described, coupling features (222, 228, 230, 244) of proximal coupler (212), tube (214), and distal coupler (216) may include at least one snap fitting (not shown) or bayonet coupling.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an end effector comprising first and second jaws, wherein the first jaw is movable relative to the second jaw; and (b) a shaft extending proximally from the end effector, wherein the shaft comprises: (i) a proximal coupler having proximal and distal ends, wherein the proximal coupler includes a distal coupling feature adjacent the distal end, (ii) a tube having proximal and distal ends, wherein the tube includes: (A) a proximal coupling feature adjacent the proximal end of the tube, wherein the proximal coupling feature is configured to engage the distal coupling feature of the proximal coupler to securably lock the tube and the proximal coupler together, and (B) a distal coupling feature adjacent the distal end of the tube, and (iii) a distal coupler having proximal and distal ends, wherein the distal coupler includes a proximal coupling feature adjacent the proximal end of the distal coupler, wherein the proximal coupling feature of the distal coupler is configured to engage the distal coupling feature of the tube to securably lock the distal coupler and the tube together.

Example 2

The instrument of Example 1, wherein the average diameter of the proximal coupler is greater than the average diameter of the tube, wherein the average diameter of the distal coupler is greater than the average diameter of the tube.

Example 3

The instrument of Examples 1 or 2, wherein the distal coupling feature of the proximal coupler or the proximal coupling feature of the tube includes a projection formed on an outer surface that is configured to lockingly engage a channel of the other of the distal coupling feature of the proximal coupler or the proximal coupling feature of the tube.

Example 4

The instrument of Example 3, wherein the channel includes a ramp that is configured move the projection from an unlocked configuration to a locked configuration, wherein the ramp is configured to prevent the projection moving back to the unlocked configuration.

Example 5

The instrument of Example 4, wherein the ramp spans across the entire width of the channel.

Example 6

The instrument of any one or more of Examples 3 through 5, wherein the distal coupling feature of the proximal coupler or the proximal coupling feature of the tube includes a second projection formed on the outer surface that is configured to lockingly engage a second channel of the other of the distal coupling feature of the proximal coupler or the proximal coupling feature of the tube.

Example 7

The instrument of Example 6, wherein the distal coupling feature of the proximal coupler or the proximal coupling feature of the tube includes a third projection formed on the outer surface that is configured to lockingly engage a third channel of the other of the distal coupling feature of the proximal coupler or the proximal coupling feature of the tube, wherein the first, second and third projections are circumferentially spaced.

Example 8

The instrument of any one or more of Examples 1 through 7, wherein the distal coupling feature of the tube or the proximal coupling feature of the distal coupler includes a projection formed on an inner surface that is configured to lockingly engage a channel of the other of the distal coupling feature of the tube or the proximal coupling feature of the distal coupler.

Example 9

The instrument of Example 8, wherein the channel includes a ramp that is configured move the projection from an unlocked configuration to a locked configuration and further prevent the projection moving to back the unlocked configuration.

Example 10

The instrument of any one or more of Examples 1 through 9, wherein the proximal coupler, the tube, and the distal coupler are tubular and have hollow interior cavities.

Example 11

The instrument of any one or more of Examples 1 through 10, wherein the proximal end of the distal coupler circumferentially overlies at least a portion of the distal coupling feature of the tube.

Example 12

The instrument of any one or more of Examples 1 through 11, wherein the proximal coupler is formed from a polymeric material, the tube is formed of a metallic material, and the distal coupler is formed from a polymeric or metallic material.

Example 13

The instrument of any one or more of Examples 1 through 12, wherein the tube is formed from a rolled metallic sheet and welded to form a tubular shape.

Example 14

The instrument of any one or more of Examples 1 through 13, wherein an outer surface of the distal coupler is smooth and continuous.

Example 15

The instrument of any one or more of Examples 1 through 14, wherein the distal coupler further comprises first and second arms projecting from the distal end of the distal coupler, wherein the first arm includes a first aperture and the second arm includes a second aperture, wherein the instrument includes at least one closure link, wherein the closure link includes a body and first and second pins extending from the body, wherein outer surfaces of the first and second pins define the length of the body of the closure link, wherein the first pin of the closure link is configured to be received within the first aperture of the distal coupler.

Example 16

A surgical instrument comprising: (a) an end effector comprising first and second jaws, wherein the first jaw is movable relative to the second jaw; (b) a shaft extending proximally from the end effector, wherein the shaft comprises an aperture at a distal end; and (c) at least one closure link configured to rotatably couple the distal coupler and the end effector, wherein the closure link comprises: (i) a body having proximal and distal most ends, (ii) a first pin extending from the body and disposed at the proximal most end of the body, wherein the first pin of the closure link is configured to be received within the aperture of the shaft, and (iii) a second pin extending from the body and disposed at the distal most end of the body.

Example 17

The instrument of Example 16, wherein outer surfaces of the first and second pins define the length of the body between the proximal and distal most ends of the closure link.

Example 18

The instrument of Examples 16 or 17, wherein the shaft comprises a proximal coupler having proximal and distal ends, a tube having proximal and distal ends, wherein the distal end of the proximal coupler is selectively coupled with the proximal end of the tube, and a distal coupler having proximal and distal ends, wherein the distal end of the tube is selectively coupled with the proximal end of the distal coupler, wherein the distal coupler comprises at least one arm projecting from the distal end of the distal coupler, wherein the arm includes an aperture.

Example 19

A method of manufacturing a closure tube of a surgical instrument, wherein the closure tube comprises a proximal coupler, a tube, and a distal coupler, the method comprising: (a) forming the proximal coupler of the surgical instrument from a polymeric material, wherein the proximal coupler includes at least one coupling feature; (b) forming at least one coupling feature into a metallic sheet; (c) rolling the metallic sheet to form a metallic tubular structure; (d) welding the metallic tubular structure to form the tube of the surgical instrument; (e) forming a distal coupler of the surgical instrument using metal injection molding or a plastic forming process, wherein the distal coupler includes at least one coupling feature; and (f) coupling the proximal coupler to the tube and the distal coupler to the tube using the coupling features of the proximal coupler, the tube, and the distal coupler.

Example 20

The method of Example 19, wherein the coupling features of the proximal coupler, the tube and the distal coupler include at least one snap fitting or bayonet coupling.

IV. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc. of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument comprising:
  (a) an end effector comprising first and second jaws, wherein the first jaw is movable relative to the second jaw; and
  (b) a shaft extending proximally from the end effector, wherein the shaft comprises:

(i) a proximal coupler having proximal and distal ends, wherein the proximal coupler includes a distal coupling feature adjacent the distal end,
(ii) a tube having proximal and distal ends, wherein the tube includes:
  (A) a proximal coupling feature adjacent the proximal end of the tube, wherein the proximal coupling feature is configured to rotatably engage the distal coupling feature of the proximal coupler at a first connection to securably lock the tube and the proximal coupler together from a first unlocked configuration to a first locked configuration, and
  (B) a distal coupling feature adjacent the distal end of the tube, and
(iii) a distal coupler having proximal and distal ends, wherein the distal coupler includes a proximal coupling feature adjacent the proximal end of the distal coupler, wherein the proximal coupling feature of the distal coupler is configured to rotatably engage the distal coupling feature of the tube at a second connection to securably lock the distal coupler and the tube together from a second unlocked configuration to a second locked configuration.

2. The instrument of claim 1, wherein the distal coupling feature of the proximal coupler or the proximal coupling feature of the tube includes a projection formed on an outer surface that is configured to lockingly engage a channel of the other of the distal coupling feature of the proximal coupler or the proximal coupling feature of the tube.

3. The instrument of claim 2, wherein the channel includes a ramp that is configured move the projection from the first or second unlocked configuration to the first or second locked configuration, wherein the ramp is configured to prevent the projection from moving back to the first or second unlocked configuration.

4. The instrument of claim 3, wherein the ramp spans across the entire width of the channel.

5. The instrument of claim 2, wherein the distal coupling feature of the proximal coupler or the proximal coupling feature of the tube includes a second projection formed on the outer surface that is configured to lockingly engage a second channel of the other of the distal coupling feature of the proximal coupler or the proximal coupling feature of the tube.

6. The instrument of claim 5, wherein the distal coupling feature of the proximal coupler or the proximal coupling feature of the tube includes a third projection formed on the outer surface that is configured to lockingly engage a third channel of the other of the distal coupling feature of the proximal coupler or the proximal coupling feature of the tube, wherein the first, second and third projections are circumferentially spaced.

7. The instrument of claim 1, wherein the distal coupling feature of the tube or the proximal coupling feature of the distal coupler includes a projection formed on an inner surface that is configured to lockingly engage a channel of the other of the distal coupling feature of the tube or the proximal coupling feature of the distal coupler.

8. The instrument of claim 7, wherein the channel includes a ramp that is configured move the projection from the first or second unlocked configuration to the first or second locked configuration and further prevent the projection from moving back to the first or second unlocked configuration.

9. The instrument of claim 1, wherein the proximal coupler, the tube, and the distal coupler are tubular and have hollow interior cavities.

10. The instrument of claim 1, wherein the proximal end of the distal coupler circumferentially overlies at least a portion of the distal coupling feature of the tube.

11. The instrument of claim 1, wherein the proximal coupler is formed from a polymeric material, the tube is formed of a metallic material, and the distal coupler is formed from a polymeric or metallic material.

12. The instrument of claim 1, wherein the tube is formed from a rolled metallic sheet and welded to form a tubular shape.

13. The instrument of claim 1, wherein the distal coupler further comprises first and second arms projecting from the distal end of the distal coupler, wherein the first arm includes a first aperture and the second arm includes a second aperture, wherein the instrument includes at least one closure link, wherein the closure link includes a body and first and second pins extending from the body, wherein outer surfaces of the first and second pins define the length of the body of the closure link, wherein the first pin of the closure link is configured to be received within the first aperture of the distal coupler.

14. A surgical instrument comprising:
(a) an end effector comprising first and second jaws, wherein the first jaw is movable relative to the second jaw;
(b) a shaft extending proximally from the end effector, wherein the shaft comprises an aperture and a recessed portion at a distal end; and
(c) at least one closure link configured to rotatably couple the shaft and the end effector, wherein the closure link comprises:
  (i) a body having proximal and distal most tips defined by opposing proximal and distal sides, wherein a portion of the body is configured to be received within the recessed portion of the shaft,
  (ii) a first pin extending from the body, wherein the first pin includes a proximal end that extends continuously along the proximal side of the body, wherein the first pin of the closure link is configured to be received within the aperture of the shaft, and
  (iii) a second pin extending from the body and terminating at the distal most tip of the body.

15. The instrument of claim 14, wherein the shaft comprises:
(a) a proximal coupler having proximal and distal ends,
(b) a tube having proximal and distal ends, wherein the distal end of the proximal coupler is selectively coupled with the proximal end of the tube, and
(c) a distal coupler having proximal and distal ends, wherein the distal end of the tube is selectively coupled with the proximal end of the distal coupler, wherein the distal coupler comprises at least one arm projecting from the distal end of the distal coupler, wherein the arm includes an aperture.

16. The instrument of claim 14, wherein the recessed portion of the shaft has a curvilinear shape, wherein the portion of the body configured to be received within the recessed portion of the shaft has a curved proximal side configured to restrict rotational movement of the closure link relative to the shaft.

17. A surgical instrument comprising:
(a) an end effector comprising first and second jaws, wherein the first jaw is movable relative to the second jaw; and (b) a shaft extending proximally from the end effector, wherein the shaft comprises:
  (i) a proximal coupler having proximal and distal ends, wherein the proximal coupler includes a distal coupling feature adjacent the distal end,
  (ii) a tube having proximal and distal ends, wherein the tube is formed from a different material than the proximal coupler, wherein the average outer diameter of the tube is less than the average outer diameter of the proximal coupler, wherein the tube includes:
    (A) a proximal coupling feature adjacent the proximal end of the tube, wherein the proximal coupling feature is configured to engage the distal coupling feature of the proximal coupler to securably lock the tube and the proximal coupler together, and
    (B) a distal coupling feature adjacent the distal end of the tube, and
  (iii) a distal coupler having proximal and distal ends, wherein the average diameter of the distal coupler is greater than the average diameter of the tube, wherein the distal coupler includes a proximal coupling feature adjacent the proximal end of the distal coupler, wherein the proximal coupling feature of the distal coupler is configured to engage the distal coupling feature of the tube to securably lock the distal coupler and the tube together, wherein the distal coupling feature of the tube or the proximal coupling feature of the distal coupler includes a projection configured to lockingly engage a channel of the other of the distal coupling feature of the tube or the proximal coupling feature of the distal coupler, wherein the channel includes a ramp that is configured move the projection from an unlocked configuration to a locked configuration and further prevent the projection from moving back to the unlocked configuration.

18. The instrument of claim 17, wherein the proximal coupling feature is configured to rotatably engage the distal coupling feature of the proximal coupler to securably lock the tube and the proximal coupler together, and wherein the proximal coupling feature of the distal coupler is configured to rotatably engage the distal coupling feature of the tube to securably lock the distal coupler and the tube together.

19. The instrument of claim 17, wherein the proximal coupler is formed from a polymeric material, the tube is formed of a metallic material, and the distal coupler is formed from a polymeric or metallic material.

20. The instrument of claim 17, wherein the projection is formed on an inner surface of the distal coupling feature of the tube or an inner surface of the proximal coupling feature of the distal coupler.

* * * * *